US009724454B2

United States Patent
Yamashita

(10) Patent No.: US 9,724,454 B2
(45) Date of Patent: Aug. 8, 2017

(54) MANUAL BREAST PUMP

(71) Applicant: PIGEON CORPORATION, Tokyo (JP)

(72) Inventor: Daisuke Yamashita, Tokyo (JP)

(73) Assignee: PIGEON Corporation, Tokyo (JP)

(*) Notice: Subject to any disclaimer, the term of this patent is extended or adjusted under 35 U.S.C. 154(b) by 0 days.

(21) Appl. No.: 14/761,532

(22) PCT Filed: Jan. 17, 2013

(86) PCT No.: PCT/JP2013/050819
§ 371 (c)(1),
(2) Date: Jul. 16, 2015

(87) PCT Pub. No.: WO2014/112078
PCT Pub. Date: Jul. 24, 2014

(65) Prior Publication Data
US 2015/0335800 A1 Nov. 26, 2015

(51) Int. Cl.
*A61M 1/06* (2006.01)
*A61M 1/00* (2006.01)

(52) U.S. Cl.
CPC ............ *A61M 1/06* (2013.01); *A61M 1/0072* (2014.02)

(58) Field of Classification Search
CPC ...... A61M 1/06; A61M 1/001; A61M 1/0005; A61M 1/0023; A61M 1/0031;
(Continued)

(56) References Cited

U.S. PATENT DOCUMENTS 4,759,747 A * 7/1988 Aida ................. A61M 1/06
604/74
8,187,219 B1 * 5/2012 Chiang ............... A61M 1/06
604/73

(Continued)

FOREIGN PATENT DOCUMENTS

CN 101232909 A 7/2008
JP 4413231 B2 2/2010
(Continued)

Primary Examiner — Nathan R Price
Assistant Examiner — John Doubrava
(74) Attorney, Agent, or Firm — Muncy, Geissler, Olds & Lowe, P.C.

(57) ABSTRACT

[Problem] To provide a manual breast pump which can be disassembled and assembled easily for cleaning purposes, and which can easily change a negative pressure during expression of milk which is generated by an operating section.

[Means for Solving] It is provided an accommodating vessel 11 for storing breast milk, a breast pump main body 21, and a manual operating section 61 attached to the breast pump main body and deforming a negative pressure generating member 30 installed on the breast pump main body. The manual operating section 61 has a lever shape, and has an engagement structure 80 which engages with the engaging section 38 on the breast pump main body 21 side. The engagement structure 80 tilts down the extending section erected in the form of a pillar, the extending section being a part of the negative pressure generating member, and is selectively engaged with a plurality of engaging sections provided in the middle of the extending section upon erecting the extending section.

5 Claims, 6 Drawing Sheets

(58) Field of Classification Search
CPC .. A61M 1/0037; A61M 1/0066; A61M 1/007; A61M 1/0074
USPC .......................................................... 604/74
See application file for complete search history.

(56) References Cited

U.S. PATENT DOCUMENTS

| | | | | |
|---|---|---|---|---|
| 9,044,534 | B2* | 6/2015 | Behrens | A61M 1/06 |
| 2004/0249340 | A1* | 12/2004 | Britto | A61M 1/06 604/74 |
| 2005/0015045 | A1* | 1/2005 | Tashiro | A61M 1/06 604/74 |
| 2005/0159701 | A1* | 7/2005 | Conaway | A61M 1/06 604/74 |
| 2007/0078383 | A1* | 4/2007 | Tashiro | A61M 1/06 604/74 |
| 2007/0191763 | A1* | 8/2007 | Nueesch | A61M 1/06 604/74 |
| 2008/0195039 | A1* | 8/2008 | Kataoka | A61M 1/06 604/74 |
| 2010/0262072 | A1* | 10/2010 | Attolini | A61M 1/0031 604/74 |
| 2014/0094747 | A1* | 4/2014 | Hirata | A61M 1/06 604/74 |
| 2014/0100520 | A1* | 4/2014 | Yamashita | A61M 1/06 604/74 |

FOREIGN PATENT DOCUMENTS

| | | | |
|---|---|---|---|
| JP | 2012-223495 | A | 11/2012 |
| WO | 2009/063338 | A1 | 5/2009 |

* cited by examiner

F I G. 2
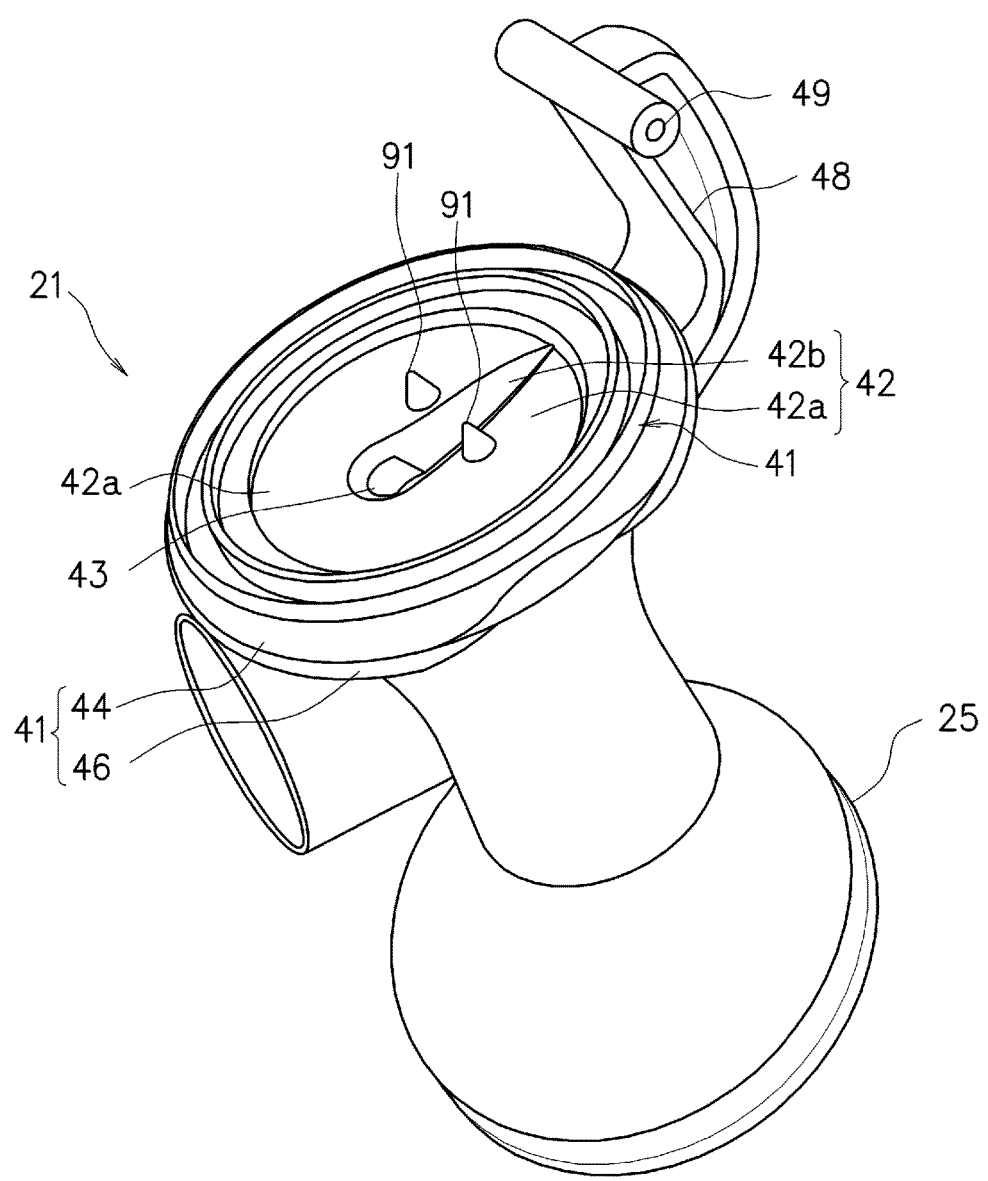

F I G. 9
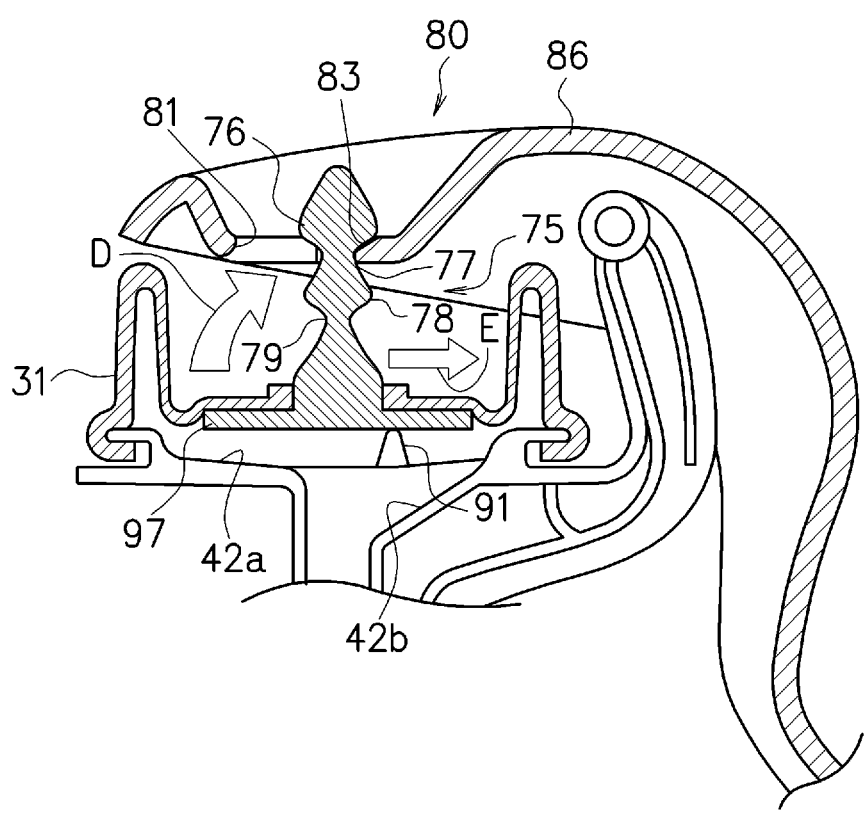

MANUAL BREAST PUMP

CROSS REFERENCE TO RELATED APPLICATIONS

This application is a national stage of International Application No.: PCT/JP2013/050819, which was filed on Jan. 17, 2013, and which is herein incorporated by reference.

TECHNICAL FIELD

The present invention relates to the improvement of a manual breast pump capable of expressing milk by generating a negative pressure by a lever-shaped operating section which is manually operated.

BACKGROUND FIELD

A breast pump has been widely used which is provided with a milk expressing section having a diameter enlarged into a trumpet shape which is abutted against a mother's breast, i.e., an enlarged-diameter milk expressing section.

In particular, a structure is known in which a recess is provided on an upper end and the like of a breast pump main body, in such a manner that breast milk which has turned into a mist due to the negative pressure during expression of milk does not leak out externally, and a deforming member, such as a diaphragm, is accommodated inside this recess.

More specifically, a manual breast pump has been known in which an operating section such as a handle is coupled to the diaphragm, and a negative pressure is generated by repeatedly lifting up the diaphragm by reciprocal movement of the handle. As a manual breast pump of this type, there is the breast pump of Japanese Patent No. 4413231 offered by the applicants (Patent Document 1).

The breast pump according to Patent Document 1 can be disassembled and assembled easily for cleaning, whereas the operating section cannot been removed easily when operated.

Consequently, this breast pump has an accommodating vessel 11 for storing breast milk, a breast pump main body 21, and a handle 61 which is attached to the breast pump main body 21 and functions as an operating section for deforming a negative pressure generating member 30 installed on the breast pump main body. An engaged structure 62 which is positioned at one end of the handle 61 moves reciprocally up and down as indicated by an arrow B due to rotating about an axle section 49, as shown in FIG. 2 of Patent Document 1.

Here, as shown in FIG. 1 of Patent Document 1, when a user operates the lever section 63 in the direction A2, i.e., so as to approach a bottle 11, and the engagement structure 62 thereby moves in the direction of an arrow B2, then a second wall section 32, which is a deforming section of the negative pressure generating member 30, is caused to deform so as to face towards the upper side from a state facing towards the lower side in FIG. 1. Therefore, when the volume of the internal space S formed between a bottom surface section 33 and an inclined surface 42 is increased, air from a milk expressing section air flow path 23 is drawn in, in accordance with the amount of air drawn into the internal space S, and when a user's breast is abutted against the enlarged-diameter front end of the milk expressing section 22, a hermetic space which is an internal space is formed, and therefore the milk expressing section air flow path 23 assumes a negative pressure. Milk is expressed by this negative pressure.

CONVENTIONAL ART DOCUMENTS

Patent Documents

Patent Document 1: Japanese Patent No. 4413231

SUMMARY OF THE INVENTION

Problems to be Solved by the Invention

By the way, in the breast pump according to Patent Document 1, the magnitude of the negative pressure used for expressing milk is dependent on the stroke of the reciprocal movement of the lever section 63.

Here, in the invention according to Patent Document 1, as shown in FIG. 8 thereof, engaging sections are formed in a plurality of locations in the length direction of an extending section 37a which extends from a boss section 37 of a coupling section 35-1.

In this case, three engaging sections, i.e., a first engaging section 38-1, a second engaging section 38-2, and a third engaging section 38-3 are formed, along a direction away from a position close to the boss section 37.

Then, an engaged section 62 on the front end of the handle 61 shown in FIG. 4 is alternatively coupled to each of the engaging sections. Consequently, the engaged section 62 of the handle 61 is coupled at the respective height positions of the first positions L1, L2, L3, in accordance with the height positions of the respective engaging sections to be engaged. Therefore, the stroke of the reciprocal movement along an arrow B in FIG. 2 changes, and hence the user is able to select a suitable strength in accordance with the magnitude of the negative pressure generated.

However, when the applicants made a trial manufacture of the structure of third engaging section 38-3 in actual practice, satisfactory results were not necessarily obtained.

This is because the task of selectively engaging the engaged section 62 on the front end of the handle 61 with any one of these three engaging sections, i.e., the first engaging section 38-1, the second engaging section 38-2 and the third engaging section 38-3, on the inner side of the deforming section 32 which is only a narrow space, when in a concave depressed state, requires the handle to be pulled out from the bearing section of the main body, and to be engaged again in another position, and therefore further modifications are necessary in order to achieve a practicable structure.

The present invention is made to solve the problems described above. An object thereof is to provide a manual breast pump which can be disassembled and assembled easily for cleaning purposes, and which can easily change the negative pressure during expression of milk which is generated by the lever-shaped operating section.

Means to Solve the Problem

In order to achieve the object described above, the present invention provides a manual breast pump having an accommodating vessel for storing breast milk, a breast pump main body attached to and detached from the accommodating vessel, and a manual operating section attached to the breast pump main body and deforming a negative pressure generating member installed on the breast pump main body, characterized in that the breast pump main body has an enlarged-diameter milk expressing section having an enlarged diameter for abutting against a user's breast; the negative pressure generating member comprises an extending section extending and erected in the form of an axle, a coupling section which is engaged with the operating section, and a deforming section which generates the negative pressure by deforming, upon receiving a force from the coupling section; the coupling section has the extending section extending and erected in the form of an axle; the manual operating section is a long handle and comprises a bearing section supported on an axle section provided on the breast pump main body; a lever section which is disposed at one end of the handle; and an engagement structure which is disposed at the other end and engaged with the coupling section; the extending section further comprises a plurality of engaging sections along the direction extending the extending section; each of the engaging sections having large diameter section having a large axis diameter and a small diameter section having a small axis diameter; at least the extending section can be tilted in the direction extending the axle; and the engagement structure of the manual operating section comprises an abutting section which abuts against the small diameter section of the extending section, and an insertion section which is provided to lead in succession to the abutting section to pass the large diameter section therethrough.

According to the structure described above, in the breast pump according to the present invention, the enlarged-diameter milk expressing section is closed off when abutted against a user's breast, and a negative pressure for expressing milk is generated inside the enlarged-diameter milk expressing section by operating the lever section in this state.

Here, in the negative pressure generating member, the deforming section is deformed by movement of the handle which is provided with the engagement structure that is engaged by the engaging section, so that a negative pressure is generated.

By the way, it has become more apparent that, in order to draw out breast milk without undue force when starting to express milk, at first, a weak negative pressure is applied in the vicinity of nipple and areola, and as the user gradually becomes used to the suctioning stimulus on the vicinity of nipple and areola, so that discharge of milk can be promoted without undue force. Furthermore, there are individual differences between the negative pressures that can be used effectively to express milk.

In view of these points, in the present invention, the extending section is tilted with regard to a plurality of engaging sections provided in the extending section of the negative pressure generating member only by operation of the lever section, so that the engaging section can pass through the insertion section to move the engagement structure to the desired engaging section, and also the abutting section can be abutted against the engaging section to generate a desired negative pressure.

Preferably, it is characterized in that each of the engaging section has the axle diameter which enlarges gradually as going downward to reach the largest diameter section where the large diameter section is formed, and then reduces gradually as further going downward to reach the smallest diameter section where the small diameter section is formed.

According to the structure described above, the engagement structure of the handle can smoothly move the extending section in the axial direction while tilting the extending section, so as to be able to easily engage with the engaging section at a desired location.

Preferably, it is characterized in that the coupling section comprises the extending section, and a planar base section expanded on the lower portion of extending section, and a mounting section of the breast pump main body to which the negative pressure generating member is installed is provided with a projecting section so that the projecting section is abutted against the lower surface of the base section.

According to the structure described above, since the lower surface of the base section is prevented from coming into intimate contact with the mounting section at surfaces, the resistance at the time of tilting the coupling section is reduced, and the movement of the engagement structure can facilitate the movement of the abutting section of the engaging section through the insertion section.

Preferably, it is characterized in that the abutting section of the engagement structure is a small-diameter through hole; the insertion section is a large-diameter through hole having larger diameter which is formed to lead to the small-diameter through hole; and a front inclined surface is formed on the upper side of the peripheral edge of the small-diameter through hole, and a backside inclined surface is formed on the backside on the peripheral edge of the large-diameter through hole.

According to the structure described above, the large diameter section cannot pass through the small-diameter through hole when the engagement structure is pressed against the extending section, and thus the extending section is tilted so that the large diameter section can be abutted against the backside inclined surface so as to be guided and moved to the large-diameter through hole, thereby passing therethrough.

Furthermore, when the large diameter section is inserted into the insertion section and then erected, the front inclined surface of the small-diameter through hole can receive the small diameter section in the small-diameter through hole which is the abutting section, and can be fitted to the lower surface of the large diameter section located immediately thereabove to support the engagement structure while lifted up.

Preferably, it is characterized in that the deforming section is made from an elastic material; the extending section is installed in the deforming section; and the extending section is installed on the deforming section so that, when the extending section is inclined, the energizing force is exerted due to elasticity of the deforming section so as to put the extending section back to the original position.

Advantageous of the Invention

As described above, according to the present invention, it is possible to provide a manual breast pump which can be disassembled and assembled easily for cleaning purposes, and which can easily change a negative pressure during expression of milk which is generated by a lever-shaped operating section.

BRIEF DESCRIPTION OF THE DRAWINGS

FIG. 2 is a schematic perspective view of a part of a breast pump main body in FIG. 1 as viewed from above.

FIG. 9 is an explanatory view showing in sequence the procedure of fixedly engaging the operating section with the engaging section of the extending section in the breast pump in FIG. 1.

DESCRIPTION OF EMBODIMENTS

Preferred embodiments of the present invention will be described below in detail with reference to the accompanying drawings.

In addition, the embodiments described below are preferred specific examples of the present invention. Therefore, although various technically desirable limitations are given, the range of the present invention is not limited to those aspects, unless it is specifically stated in the description given below that the present invention is limited.

Figure 1:
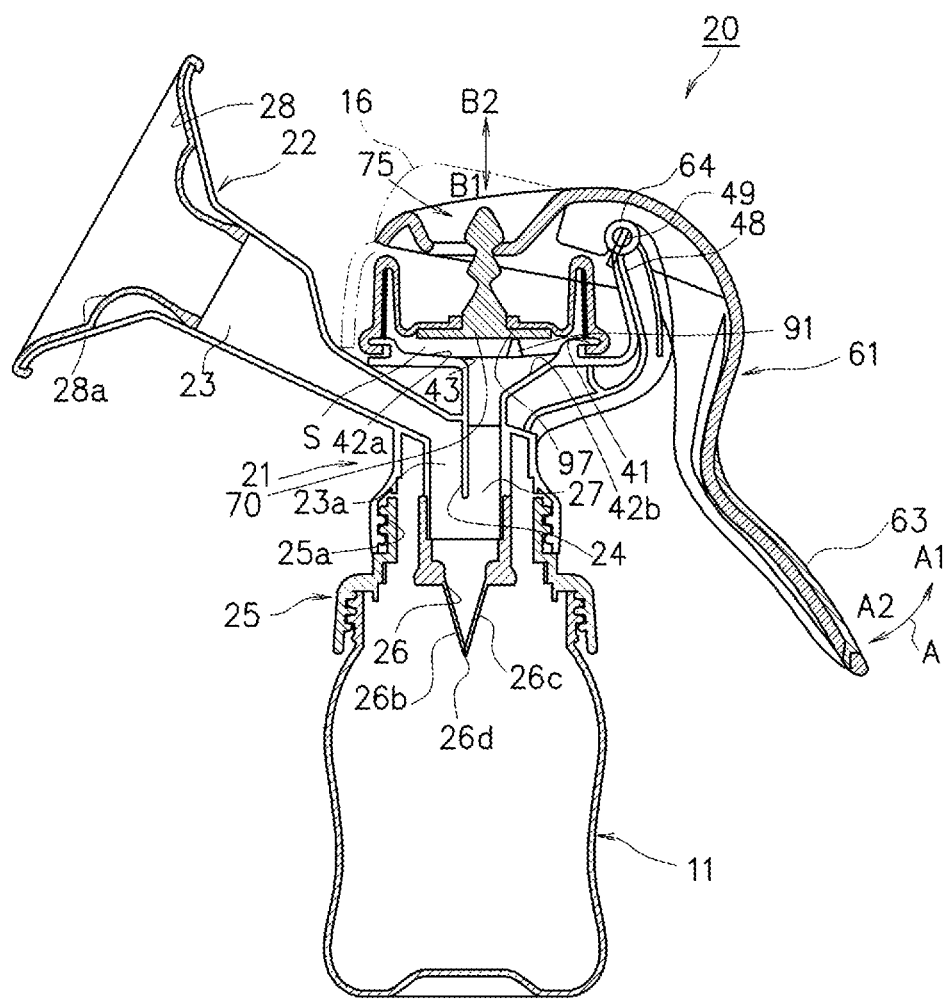
FIG. 1 is a schematic cross sectional view of a breast pump according to an embodiment of the present invention.

FIG. 1 is a schematic perspective view of a breast pump according to an embodiment of the present invention (hereinafter referred to as "breast pump"), and FIG. 2 is a general perspective view of only a breast pump main body as viewed from above.

In these drawings, the breast pump 20 is provided with a breast pump main body 21 (hereinafter referred to as "main body" below), a handle 61 which is an operating section, and a bottle 11 which is an accommodating vessel for storing the expressed breast milk. The handle 61 can be attached to and detached from the breast pump main body 21 at the position of an axle section 49.

The handle 61 which is an operating section can be rotated at a prescribed angle about the axle section 49.

More specifically, a user operates a lever section 63 at one end side of the handle 61 in a reciprocating manner like arrows A1 and A2, so that the other end of the handle 61 is rotated and a deforming section described below is deformed, thereby generating a negative pressure to express milk. The feature in which it is possible to easily change a stroke width of rotation of the handle 61 in the reciprocating operation is the characteristic of the embodiment described below.

Furthermore, as shown in FIG. 1, a negative pressure generating member 30 described below is mounted on an upper section of the main body 21. Furthermore, a substantially dome-shaped hood 16 may be attached and detached to and from an upper section thereof.

The hood 16 is cut out in the location of the handle 61 and can cover and protect the negative pressure generating member 30, or the like, by being installed so as to avoid the handle 61. It is also possible to adopt a structure which does not include the hood 16.

The whole of the main body 21 is made from synthetic resin material which is relatively light and robust; for example, the main body 21 is made from polypropylene, polycarbonate, polycycloolefin, polyethersulfone, polyphenylsulfone, or the like.

The main body 21 is provided with an attachment and detachment section 25 for attaching to and detaching from the bottle 11. The attachment and detachment section 25 is, for example, a flat tubular portion as shown in FIG. 1, which has a female thread section 25a on the inner side, so as to threadedly engage with a male thread section formed on the circumference of a mouth of the bottle 11.

In addition, the bottle 11 may be a product dedicated to the breast pump 20 or may use a feeding bottle which is compatible with the attachment and detachment section 25, or may be a bag-shaped member, rather than a formed vessel.

As shown in FIG. 1, a conical or trumpet-shaped enlarged-diameter milk expressing section 22 having a front end which opens to a large diameter is provided in an obliquely inclined state on top of the attachment and detachment section 25 of the main body 21. A shock absorbing section 28, which is an elastic body made of silicone rubber, elastomer, natural rubber, or the like, is attached detachably to the opening side of the enlarged-diameter milk expressing section 22. The shock absorbing section 28 reduces the stimulus produced due to the abutment of the enlarged-diameter milk expressing section 22 against the breast during expression of milk, so as not to cause pain. A projecting section 28a which applies a stimulus to the vicinity of the areola of the user is formed at a plurality of locations, e.g., in two positions on the upper and lower sides, on the inner circumferential surface of the shock absorbing section 28.

The milk expressing section air flow path 23 of the enlarged-diameter milk expressing section 22 serves as a flow path for air and expressed breast milk, which bends downwards towards the bottle 11. Furthermore, an opening on the bottle 11 side of the milk expressing section air flow path 23 of the enlarged-diameter milk expressing section 22 is located on the inner side of the attachment and detachment section 25 between the main body 21 and the bottle 11, and a small chamber 26 is attached thereto. Moreover, another air flow path 27 is provided via a partition wall 24, adjacently to a downward facing portion 23a of the milk expressing section air flow path 23. As shown in the figures, the lower end opening of the air flow path 27 communicates with the downward facing portion 23a of the milk expressing section air flow path inside the small chamber 26.

The upper end of the air flow path 27 is an opening 43, as shown in FIGS. 1 and 2, and is formed into a mounting section 41 which enlarges in a substantially circular shape so as to surround the opening 43. The mounting section 41 is a portion where the negative pressure generating member 30 is mounted. The negative pressure generating member 30 is described in detail below.

The upper surface of the mounting section 41 is formed as an inclined surface 42 which is inclined so as to descend slightly towards the opening 43.

As shown in FIGS. 1 and 2, the small chamber 26 is in the form of a hollow cup made entirely from an elastic body such as silicone rubber, an elastomer, natural rubber, etc., and both side walls 26b and 26c on the lower end side thereof are valve elements which constitute inclined walls of the elastic body that are formed to be thin and gradually approach each other towards the lower end. A slit 26d is provided on the lower end where both the side walls 26b and 26c approach each other. When a prescribed amount of expressed breast milk is stored inside the hollow in the small chamber 26, then due to the weight of the stored milk and the change in pressure when the negative pressure is released, as described below, the slit 26d opens, and the breast milk drops down inside the bottle 11. Furthermore, thanks to a slit 26d formed at the lower end of the inclined walls, the air inside the bottle 11 is prevented from entering into the small chamber 26 under the negative pressure.

Moreover, a small ventilation hole (not shown) which communicates the interior of the bottle 11 with the outside air is formed at a location adjacent to the attachment and detachment section 25 of the breast pump main body 21, so that pressure occurring when the breast milk has stored inside the bottle 11 can escape.

FIG. 2 is a general perspective view of the main body 21 as viewed from above.

The upper surface of the mounting section 41 on which the negative pressure generating member described below is attached is provided with a first inclined surface 42a which is inclined so as to descend slightly towards the opening 43, and a second inclined surface 42b which is formed partially on the upper surface of the mounting section 41 on the side of an arm 48 to which the handle as being the operating section is attached.

The second inclined surface 42b is made to be the incline sharper than the first inclined surface 42a, and is in the form of a narrow groove in which, for example, bosses 91, 91 are formed in vicinity of the middle thereof at the position across the second inclined surface 42b as projecting sections which slightly project upward.

Reference will be made concerning FIG. 3.

The negative pressure generating member 30 has a deformation member 50 which has an overall form close to that of a relatively flat round cylindrical body having a bottom.

The deformation member 50 has a first wall section 31 which is erected on an outer side and provides sufficient rigidity to maintain the outer diameter, and a second wall section 32 which is an inside wall section of which the upper end portion is bent back to the inner side in an integrated fashion, and the portion forward of the bent back portion is formed with a small thickness. The second wall section 32 is a deforming section, the lower end of which forms a bottom surface section 33, which is a relatively broad inner bottom section provided to extend in an integrated fashion so as to close off the lower portion of the round cylindrical shape.

More specifically, both the first wall section 31 and the second wall section 32 are made from the same material, but different rigidities are imparted by varying the thickness of the material. In other words, the first wall section 31 is made thicker than the second wall section 32. Therefore, when an external force is applied, the second wall section 32 is able to deform by an external force at the level that does not cause the first wall section 31 to deform. The second wall section 32 which is connected in an integrated fashion to the first wall section 31 covering the outer circumference thereof is thus arranged to the inner side in the form of a cylinder having a bottom, and ensures that a certain negative pressure is generated upon receiving an action of the operating section, as described below.

Instead of or in addition to the structure described above, it is also possible to vary the material used for the first wall section 31 and the second wall section 32, and to form the whole member by two-part molding, using a material having a lower rigidity than the first wall section for the second wall section 32.

As described below, when the handle 61 is operated, in the negative pressure generating member 30, the second wall section 32 deforms and the volume of an internal space S which is formed between the bottom surface section 33 and the mounting section 41 increases, thereby making it possible to generate a negative pressure by suctioning air inside the air flow path 27 and the milk expressing section air flow path 23.

In this case, the first wall section 31 hardly deforms at all, and hence the state of installation with respect to the mounting section 41 can be maintained.

A projecting section 51 extending in a longitudinal direction is provided on the opposing surfaces of the first wall section 31 and the second wall section 32 so as to be interposed therebetween. In FIG. 3, the projecting section 51 is formed on the inner surface side of the first wall section 31. This can effectively prevent an operating sound from becoming an unpleasant sound, the operating sound being produced when the second wall section 32, which is the deforming section, repeatedly deforms and then is restored to its original shape, and the opposing surfaces of the second wall section 32 and the first wall section 31 abut against each other during this restoring motion.

In order to deform the second wall section 32, the negative pressure generating member 30 is provided with a coupling member 70.

The coupling member 70 is made from a hard material which is different to the second wall section 32.

The coupling member 70 is made entirely from a relatively hard synthetic resin, such as polypropylene, polycarbonate, polycycloolefin, polyethersulfone, or the like, and has a disk-shaped base section 97 at the base end section, as well as an extending section 75 which is formed in an integrated fashion on top of the base section 97 and which extends in the form of an axle.

A base end section 37 is provided in the vicinity of the joining portion of the extending section 75 to the base section 97.

A clearance hole 34 is formed in a central portion of the bottom surface section 33.

More specifically, since the deformation member 50 and the coupling member 70 are formed as separate bodies, the extending section 75 of the coupling member 70 is inserted into the clearance hole 34 in the bottom surface section 33 of the deformation member 50, and then fixed at the base end section 37.

The clearance hole 34 is set to have a slightly smaller inner diameter than the outer diameter of the base end section 37, so that the base end section 37 can be inserted into the clearance hole 34 very easily, while reliably ensuring airtight properties. In this case, attachment and detachment for the purpose of cleaning, or the like, can be performed easily.

Moreover, since the deformation member 50 and the coupling member 70 are made as separate bodies, it is possible to easily achieve a structure in which the coupling member 70 rotates axially with respect to the bottom surface section 33.

Figure 3:
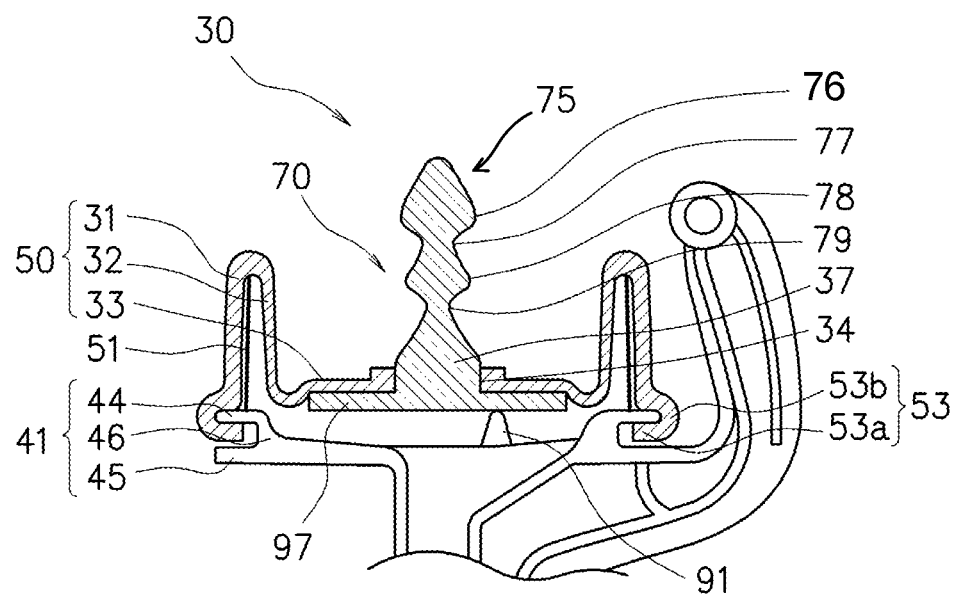
FIG. 3 is an enlarged cross sectional view of a part of a negative pressure generating member in FIG. 1.

Furthermore, as shown in FIG. 3, the negative pressure generating member 30 is attached to and detached from a peripheral edge of the mounting section 41, by an attachment and detachment section 53 which is formed in a substantially circular shape, the peripheral edge being formed with a diameter slightly larger than the attachment and detachment section 53.

The attachment and detachment section 53 has an inward facing flange 53a, which is a negative pressure generating side flange section that projects inwards at the lower end thereof, by the first wall section 31 extending downwards and being bent inwards, and an inner groove 53b which is a negative pressure generating side groove section which is formed on the upper side and the inner side of the flange 53a. The whole of the attachment and detachment section 53 has elasticity.

In contrast, an outward facing dual flange is formed on the peripheral edge section of the mounting section 41, i.e., a first flange 44 which is the upper end portion of the mounting section 41 and is an outwardly projecting main body side flange section, and a second flange 45 which is a positioning means positioned below the first flange 44 and having an outer diameter larger than the lower end of the attachment and detachment section 53 and the first flange 44. Also, an outer groove 46 which is open on the outer side is formed, the outer groove 46 being a main body side groove section that is indented to the inner side by reducing in diameter between the first flange 44 and the second flange 45.

Therefore, a user grips the side surfaces constituted by the first wall section 31 and the second wall section 32 of the negative pressure generating member 30, and causes the outer surface of the inward facing flange 53a, which is the lower end of the attachment and detachment section 53 positioned on the opposite side to the gripped position, to abut against the upper surface of the second flange 45, which is a positioning means. Then, in a state where the inward facing flange 53a is engaged inside the outer groove 46, the user pulls the negative pressure generating member 30 with her gripping hand while lightly pressing down on the engaged position with a finger of the non-gripping hand. Consequently, the inward facing flange 53a in the portion other than the engaged position deforms and rides up over the first flange 44 and enters into the main body side groove section 46. Then, the attachment and detachment section 53 entirely becomes installed to the peripheral edge of the mounting section 41, so that the first flange 44 enters into the inner groove 53b and the inward facing flange 53a also enters into the outer groove 46, whereby a installation that remains hermetically sealed is achieved.

Consequently, the negative pressure generating member 30 is installed very easily. More specifically, the second flange 45 is formed at a position which is distanced slightly further from the first flange 44 than the thickness of the inward facing flange 53a. Also, when the negative pressure generating member 30 is installed, the second flange 45 serves as a projecting rib that prevents the inward facing flange 53a from riding up over the outer groove 46.

Furthermore, on the other hand, the negative pressure generating member 30 can be removed very easily upon removing because the inward facing flange 53a is removed from the outer groove 46 and rides up over the first flange 44 by simply holding the first wall section 31 by hand and stretching outwards.

In addition, in the present embodiment, the second flange 45 has a similar shape to the first flange 44, but it may also be formed with a portion that projects beyond the first flange 44, in a part thereof; for example, it may be configured so that a cutaway is formed in a side edge so as to facilitate the action of pressing with the other finger.

Here, the first wall section 31, the second wall section 32, and the bottom surface section 33 of the deformation member 50 are preferably formed integrally in their entirety from a soft material having relatively good elasticity, i.e., a synthetic resin having a hardness of approximately HS30 to 70 as measured by an A-type durometer according to JIS-K6253 (ISO 7619), or an elastomer such as silicone rubber, isoprene rubber, or SEBS (styrene-ethylene-butylene-styrene), for example.

Moreover, it is preferable that the thickness of the material constituting the portion of the first wall section 31 is 1.5 mm to 3.0 mm, and the thickness of the material constituting the second wall section 32 is 1.0 mm to 2.5 mm.

If the hardness of the deformation member 50 is smaller than 30, then the deformation of the first wall section 31 and the generated negative pressure both become small. If the hardness exceeds 60, then the force required to operate the handle 61 as described below becomes large, and the operation for generating a negative pressure becomes very difficult.

If the thickness of the second wall section 32 is smaller than 1.0 mm, then the extension deformation due to rubber elasticity upon deformation becomes larger, and the generated negative pressure becomes smaller. If the thickness exceeds 2.5 mm, then the force required to operate the handle 61 as described below becomes large, and the operation for generating a negative pressure becomes very difficult.

If the thickness of the first wall section 31 is smaller than 1.5 mm, then the wall section will buckle during the generation of a negative pressure. More specifically, unnecessary deformation occurs and a sufficient negative pressure cannot be generated. If the thickness of the first wall section 31 exceeds 3.0 mm, then the wall section cannot deform sufficiently during mounting with the main body 21, and thus it becomes difficult to mount.

As shown in FIG. 1, in the upper portion of the main body 21, an arm 48 for attaching the handle 61, and an axle section 49 formed on the front end thereof, extend at a position opposite to the position where the enlarged-diameter milk expressing section 22 extends. The arm 48 is located at a position whereby the front end thereof is adjacent to the negative pressure generating member 30 and is located above the upper end of the negative pressure generating member 30.

The handle 61 which is the operating section is supported rotatably on the axle section 49.

The handle 61 has a long shape as shown in FIG. 1, for example, and is formed entirely in one piece made as a molded product from a relatively light and robust synthetic resin, such as polypropylene, polycarbonate, polycycloolefin, polyether sulfone, and the like.

Figure 4:
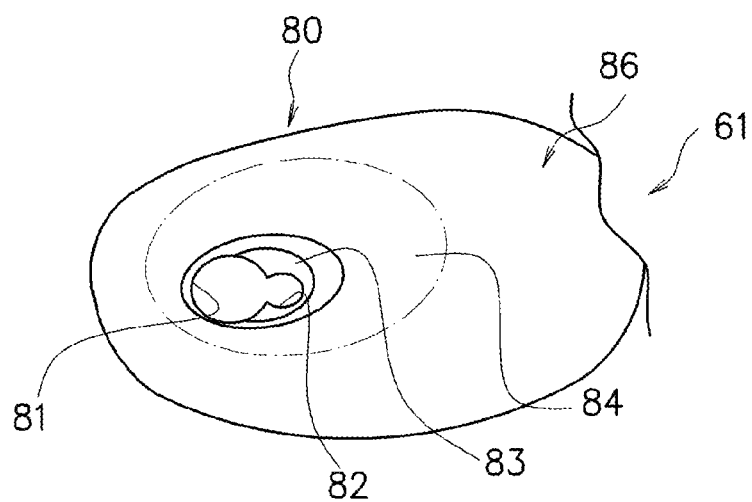
FIG. 4 is a partially enlarged perspective view of an engagement structure of an operating section of the breast pump in FIG. 1 as viewed from above.
Figure 5:
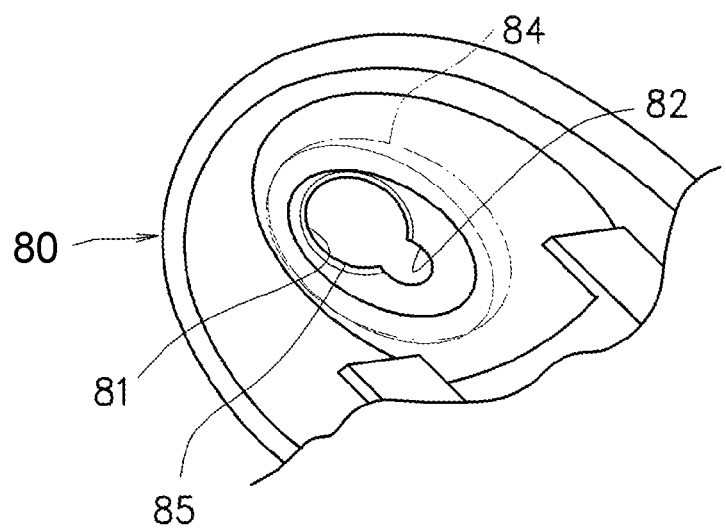
FIG. 5 is a partially enlarged perspective view of an engagement structure of an operating section of the breast pump in FIG. 1 as viewed from below.

As shown in FIG. 4, a depression 84 which is a concave portion is formed in the vicinity of the upper end 86 of the handle 61. An engagement structure 80 is provided in the depression 84. FIG. 5 is a schematic perspective view seeing the upper end of the handle from backside.

With reference to FIGS. 4 and 5, the depression 84 has a first through hole 81 as being an inserting section, and a second through hole 82 formed therein, the second through hole connected to the first through hole 84 in the lateral direction, i.e., formed in the laterally-connected state in a continuous manner to be located at the deeper side position (on the right side in FIG. 1). The first through hole 81 has a large diameter, and is formed considerably larger than the outer circumference of a large diameter section of the extending section described below so as to serve as a press-in section for inserting into the large diameter section. The second through hole 82 has a small diameter which is a size to the extent that a small diameter section of the extending section described below can enter thereinto without any gap practically.

Then, a backside inclined surface 85 is provided on the lower surface of the hole peripheral edge of the region of the first through hole 81 connecting to at least the second through hole 82, and a front inclined surface 83 is formed on the upper surface of the hole peripheral edge of the second through hole 82.

The structure of the extending section 75 will be described in detail with reference to FIG. 3.

The extending section 75 is a part of the coupling member 70, and, as shown in figure, has the form of an axle extending in the shape of a pillar in which the axis diameter is varied at a plurality of portions along the axial direction.

More specifically, the form includes portions having large axis diameter and portions having small axis diameter continuous in sequence in the lateral direction. The upper end of the extending section 75 located opposite to the base section 97 preferably has a front end which is made thinner to some extent, and the end portion is rounded taking safety into consideration.

In the extending section 75, a plurality of large diameter sections and small diameter sections is alternately formed along the vertical direction so as to constitute the engaging section.

The number of large diameter sections and that of small diameter sections are not limited to the illustrated structure, but may be set to be larger. The larger the number of provision increases, the finer the rotation stroke of the handle can be set.

In the example of the illustrated embodiment, it is possible to perform the adjustment in two levels.

A first large diameter section 76 at the top of the extending section 75 has a thin upper end. The diameter thereof enlarges gradually as going downward to reach the largest diameter section, and then reduces gradually as further going downward to reach a first small diameter section 77 which is a constricted portion.

Furthermore, stating from the first small diameter section 77, the diameter again enlarges as going downward to reach a second large diameter section 78 at the largest diameter section, and then reduces gradually as going downward to reach a second small diameter section 79.

The cross section of each of the enlarged-diameter section and the reduced-diameter section is a so-called tapered shape.

In addition, the portion of the extending section 75 where the base section 97 is joined is the base end section 37 which maintains the axial diameter approximately same as the large diameter section in the axial direction.

Having a tapered shape as described above, the extending section 75 can incline by the operation of the lever section as described below to change the position thereof, thereby being easily engaged with the engagement structure.

Here, the structure of the extending section is not limited to the tapered shape as described above, but may be the form in which the diameter is enlarged more sharply; for example, the outer shape may be exhibited in which an incline sharply changes in curve like an exponential function graph. In such a case, the extending section moves to incline and erect more rapidly.

Next, the effect of the present embodiment will be explained.

Figure 6:
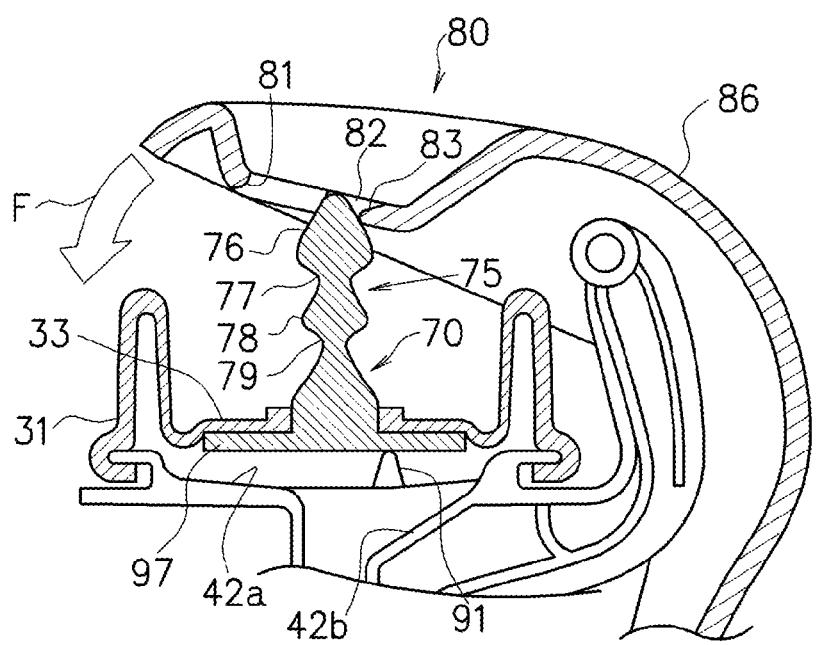
FIG. 6 is an explanatory view showing in sequence the procedure of fixedly engaging the operating section with the engaging section of the extending section in the breast pump in FIG. 1.

As shown in FIG. 6, a bearing section 64 of the handle 61 which is the operating section is fitted in the axle 49 of the arm 48 so that the handle 61 can rotate.

In this state, the upper end 86 of the handle 61 situates in the upper portion of the extending section 75.

When the lever section 63 of the handle 61 is rotated in the direction of A1 in FIG. 1, as shown in FIG. 6, the force is exerted to rotate the upper end 86 of the handle downward in the direction of an arrow F.

Consequently, the upper end 86 of the handle presses the extending section 75 from the upside to the downside. In this state, the tapered-shaped portion, which has the gradually enlarged diameter, on the upper portion of the first large diameter section 76 of the extending section 75 is abutted against the second through hole 82 of the engagement structure 80.

Figure 7:
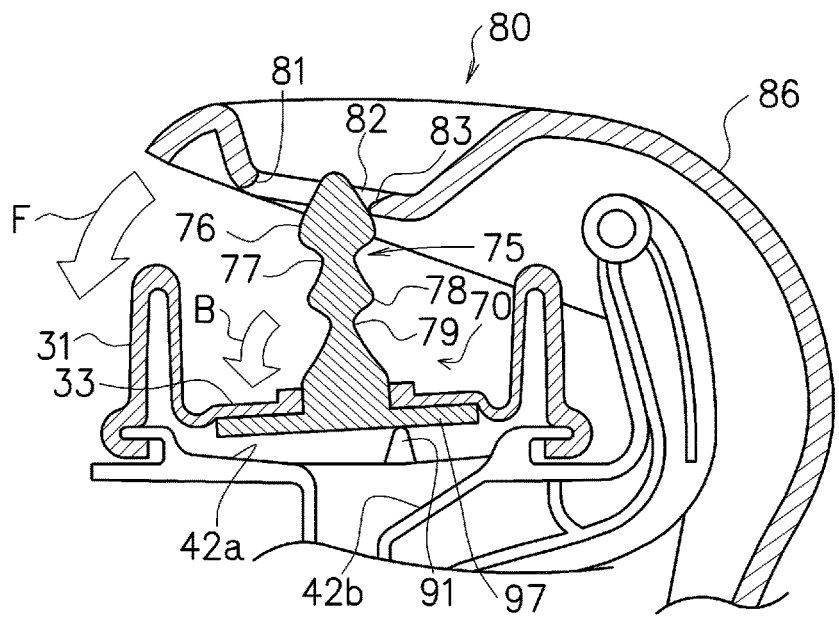
FIG. 7 is an explanatory view showing in sequence the procedure of fixedly engaging the operating section with the engaging section of the extending section in the breast pump in FIG. 1.

Furthermore, when the upper end 86 of the handle is rotated downward in the direction of an arrow F (when the lever section 63 in FIG. 1 is further moved in the direction of A1), as shown in FIG. 7, the extending section 75 is pressed toward the second through hole 82 so as to be inclined in the direction of the first through hole 81 leading to the second through hole 82 in succession.

In such an instance, the boss 91 is arranged under the base section 97 of the coupling section 70, and this facilitate inclining the extending section 75 along with the whole of the coupling section 70 in the direction of an arrow B. In such an instance, since the deforming section 31 is excellent in elasticity, the energizing force is exerted on the extending section 75 toward the direction opposite to an arrow B (in the direction of an arrow D in FIG. 9).

At this stage, in the extending section 75, the first large diameter section 76 hits the region in the vicinity of the boundary between the first through hole 81 and the second through hole 82 of the handle side engagement structure (see FIG. 3), and thus the extending section 75 is not pressed into the first through hole.

Figure 8:
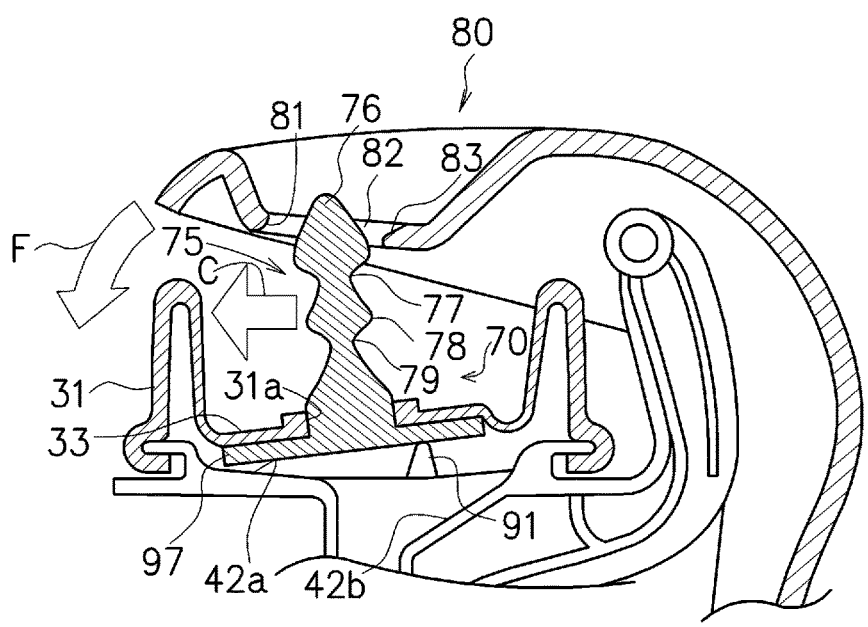
FIG. 8 is an explanatory view showing in sequence the procedure of fixedly engaging the operating section with engaging section of the extending section in the breast pump in FIG. 1.

As shown in FIG. 8, when the upper end 86 of the handle is further rotated downward in the direction of an arrow F, the extending section 75 is guided to the backside inclined surface 85, and pushed in the direction of an arrow C, i.e., the direction of the first through hole 81 so as to be shifted, so that the first through hole 81 passes through the first large diameter section 76.

Furthermore, when the upper end 86 of the handle is further rotated downward in the direction of an arrow F, as shown in FIG. 9, thanks to the first small diameter section 77 located in the engagement structure 80, the energizing force due to elasticity of the deforming section 31 is exerted on the extending section 75 in the directions of an arrow D and an arrow E, thereby restoring the incline of the extending section 75 and standing the section erect. The first small diameter section 77 is fitted into and fixedly engaged with the second through hole 82 of the engagement structure 80.

For the reasons described above, the engagement structure 80 of the handle 61 is positioned on the upper portion of the extending section 75 so that the reciprocating movement of the lever section 63 indicated by an arrow A in FIG. 1 is performed with relatively small stroke, and thus a negative pressure generated in the negative pressure generating member 30 is relatively weak.

In this regard, when the upper end 86 of the handle section is pushed in the direction of an arrow F, the engagement structure 80 passes through the second large diameter section in the same fashion as described above so that the second small diameter section 79 is fixedly engaged with the second through hole 82.

This positions the engagement structure 80 of the handle 61 on the lower portion of the extending section 75, and thus the reciprocating movement of the lever section 63 indicated by an arrow A in FIG. 1 can be performed with larger stroke. The negative pressure generated at the negative pressure generating member 30 is thus relatively strong.

Then, when the fixed engagement described above is released, a user can easily release the engagement by, for example, pressing the extending section 75 exposed from the second through hole by her fingertip, moving the extending section 75 to the side of the first through hole 81 to pass through the second large diameter section and the first large diameter section, thereby moving the upper end 86 of the handle 61 to the upper portion of the extending section 75.

In this manner, according to the present embodiment, it is possible to provide a manual breast pump which can be disassembled and assembled easily for cleaning purposes, and which can easily change the negative pressure during expression of milk which is generated by the lever-shaped operating section.

The present invention is not limited to each of the embodiments described above.

For example, the large diameter section and the small diameter section formed in the extending section are not limited two pairs including large and small ones as the above-discussed embodiments, but three large diameter sections and three small diameter sections, or further larger number of them may be provided.

Two bosses 91 are provided in a pair, however, three or more of them may be provided, and the shape thereof may be projections having the shape different from one another. Any type of aspect may be employed as long as it is the projecting section including one rib and the like which extends along the direction of alignment of the bosses 91, 91.

Furthermore, the individual structures of each embodiment are not necessarily required in their entirety, and a portion thereof can be omitted, in which case it may be possible to adopt a combination of different structures by combining other structures which are not illustrated, or to use the respective compositions of the embodiments in a mutually combined fashion.

Explanation of Reference Numerals

11 . . . Accommodating vessel, 20 . . . Breast pump, 21 . . . (Breast pump) main body, 22 . . . Enlarged-diameter milk-expressing section, 30 . . . Negative pressure generating member, 31 . . . First wall section, 32 . . . Second wall section, 33 . . . Bottom surface section, 50 . . . Deformation member, 61 . . . Handle, 63 . . . Lever section, 70 . . . Coupling member, 75 . . . Extending section, 76 . . . First large diameter section, 77 . . . First small diameter section, 78 . . . Second large diameter section, 79 . . . Second small diameter section, 80 . . . Engagement structure, 81 . . . First through hole, 82 . . . Second through hole.

The invention claimed is:

1. A manual breast pump having an accommodating vessel for storing breast milk, a breast pump main body attached to and detached from the accommodating vessel, and a manual operating section attached to the breast pump main body and deforming a negative pressure generating member installed on the breast pump main body, wherein:
the breast pump main body has an enlarged-diameter milk expressing section having an enlarged diameter for abutting against a user's breast;
the negative pressure generating member comprises:
an extending section extending and erected in the form of an axle and engaged with the manual operating section,
a deforming section which generates the negative pressure by deforming, upon receiving a force from the extending section;
a planar base section that is expanded on a lower portion of the extending section
a mounting section of the breast pump main body that is attached to the base section, and
a projecting section that is provided on the mounting section so that the projecting section is abutted against a portion of the lower surface of the base section and the extending section is configured to tilt,
the manual operating section is a long handle and comprises:
a bearing section supported on an axle section provided on the breast pump main body;
a lever section which is disposed at one end of the handle; and
an engagement structure which is disposed at the other end and engaged with the extending section;
the extending section further comprises a plurality of engaging sections along the direction extending the extending section;
each of the engaging sections having a large diameter section having a large axis diameter and a small diameter section having a small axis diameter; and
the engagement structure of the manual operating section comprises a small-diameter through hole and a large-diameter through hole having larger diameter which is formed to lead to the small-diameter through hole,
when the handle swings in one direction, the small-diameter through hole of the engagement structure is attached to the large diameter section of the extending section,
when the handle further swings in the one direction, the extending section tilts toward the large-diameter through hole, causing the large diameter section to penetrate through the large-diameter through hole, the extending section which tilts being defined as in a tilt status,
when the handle further swings after the large diameter section penetrates through the large-diameter through hole, the small-diameter section of the extending section penetrates through the large-diameter through hole, after the penetration of the small-diameter section, the extending section recovers from the tilt status, and the small-diameter through hole of the engagement structure is engaged with the small diameter section of the extending section.

2. The manual breast pump according to claim 1, wherein each of the engaging section has the axle diameter which enlarges gradually as going downward to reach the largest diameter section where the large diameter section is formed, and then reduces gradually as further going downward to reach the smallest diameter section where the small diameter section is formed.

3. The manual breast pump according to claim 1, wherein a front inclined surface is formed on the upper side of the peripheral edge of the small-diameter through hole, and a backside inclined surface is formed on the back side of the peripheral edge of the large-diameter through hole, the backside inclined surface guiding a tilt movement of the extending section.

4. The manual breast pump according to claim 1, wherein the deforming section is made from an elastic material; the extending section is installed in the deforming section; and the extending section is installed on the deforming section so that, when the extending section is inclined, an elastic force is exerted due to elasticity of the deforming section so as to put the extending section back to the original position.

5. The manual breast pump according to claim 2, wherein a front inclined surface is formed on the upper side of the peripheral edge of the small-diameter through hole, and a backside inclined surface is formed on the back side of the peripheral edge of the large-diameter through hole, the backside inclined surface guiding a tilt movement of the extending section.

\* \* \* \* \*